US010633367B2

(12) United States Patent
Cheng et al.

(10) Patent No.: US 10,633,367 B2
(45) Date of Patent: Apr. 28, 2020

(54) FLUORINE- AND/OR DEUTERIUM-CONTAINING COMPOUNDS FOR TREATING NON-SMALL CELL LUNG CANCER AND RELATED DISEASES

(71) Applicant: X-Cutag Therapeutics, Inc., Framingham, MA (US)

(72) Inventors: Changfu Cheng, Northborough, MA (US); Shuhao Wen, Andover, MA (US); Hui Joyce Li, Westborough, MA (US)

(73) Assignee: X-CUTAG THERAPEUTICS, INC., Framingham, MA (US)

( * ) Notice: Subject to any disclaimer, the term of this patent is extended or adjusted under 35 U.S.C. 154(b) by 0 days.

(21) Appl. No.: 16/149,172

(22) Filed: Oct. 2, 2018

(65) Prior Publication Data

US 2019/0169171 A1 Jun. 6, 2019

Related U.S. Application Data

(60) Provisional application No. 62/567,379, filed on Oct. 3, 2017.

(51) Int. Cl.
*C07D 403/04* (2006.01)
*C07B 59/00* (2006.01)
*A61P 35/00* (2006.01)

(52) U.S. Cl.
CPC ............ *C07D 403/04* (2013.01); *A61P 35/00* (2018.01); *C07B 59/002* (2013.01); *C07B 2200/05* (2013.01)

(58) Field of Classification Search
CPC ... A61P 35/00; C07B 2200/05; C07B 59/002; C07D 403/04
See application file for complete search history.

(56) References Cited

FOREIGN PATENT DOCUMENTS

| WO | WO 2016/029839 | * | 3/2016 | ........... C07D 401/04 |
| WO | WO 2017086830 | * | 5/2017 | ........... C07D 403/04 |

* cited by examiner

*Primary Examiner* — Erich A Leeser
(74) *Attorney, Agent, or Firm* — Wenderoth, Lind & Ponack, L.L.P.

(57) ABSTRACT

Novel fluoride and/or deuterium-containing chemical, compounds useful for treating cancer or a related disease or disorder thereof, and pharmaceutical compositions and methods of preparation and use thereof.

15 Claims, 17 Drawing Sheets

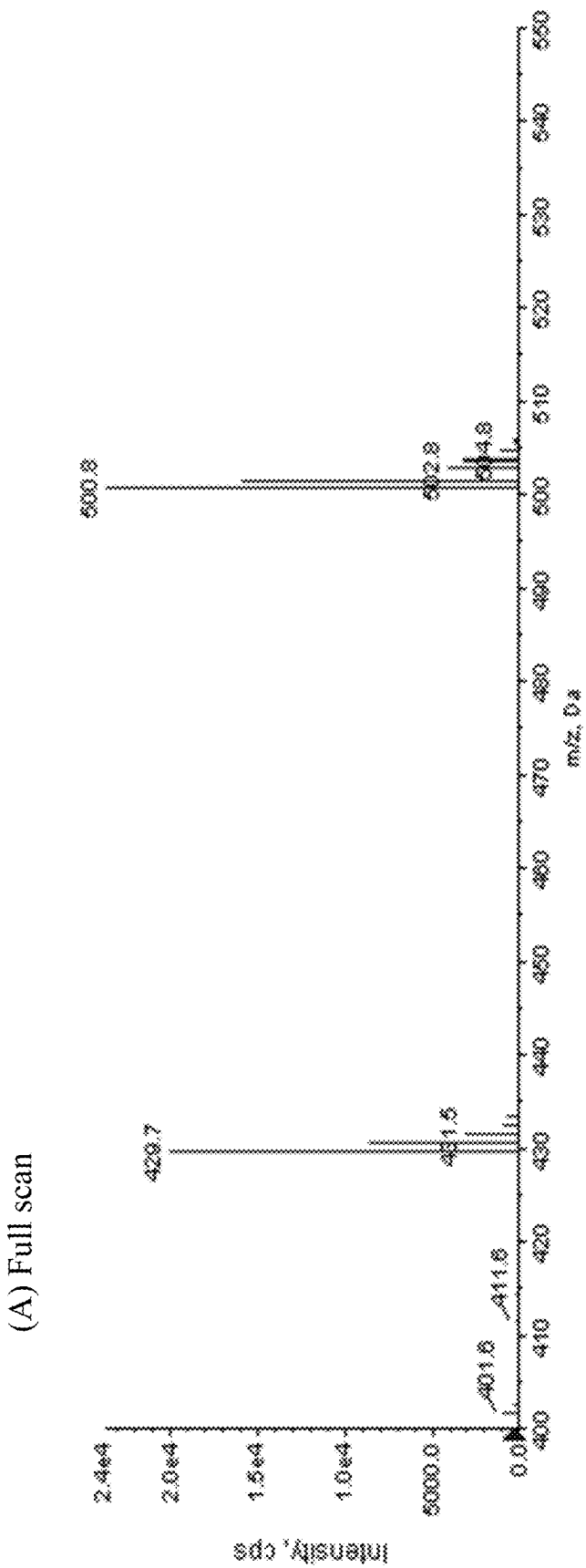
Figure 1a. Mass spectrometric analysis of osimertinib: Full-scan spectrum
(A) Full scan

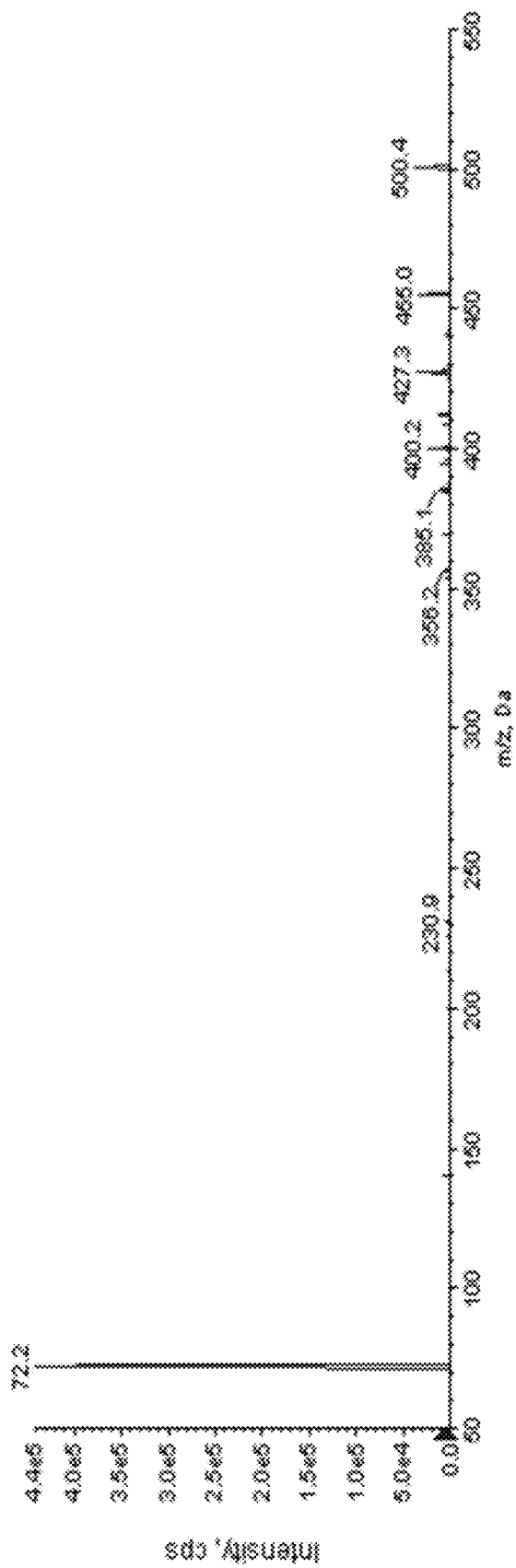
Figure 1b. Mass spectrometric analysis of osimertinib: Product-ion scan spectrum
(B) Product ion scan of protonated molecular ion (*m/z* 500.4)

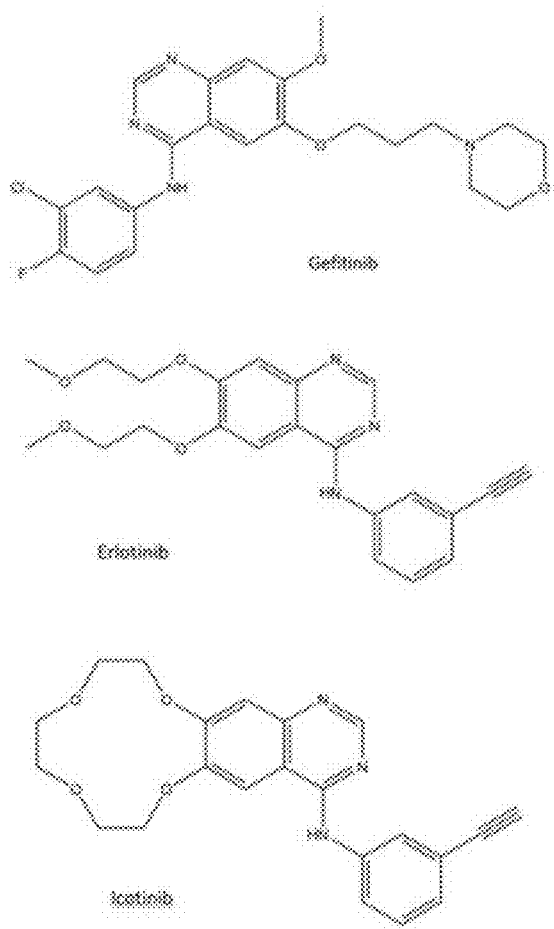
Figure 2. Chemical structures of first-generation EGFI TKIs

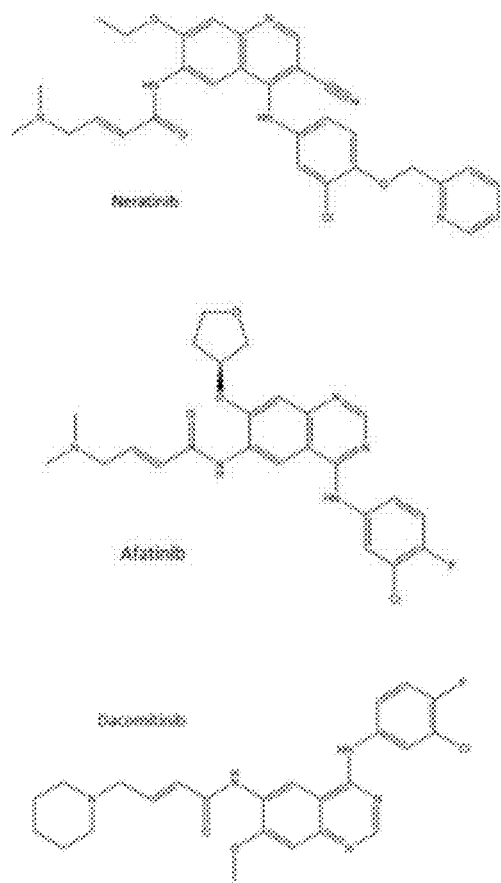
Figure 3. Chemical structures of second-generation EGFI TKIs

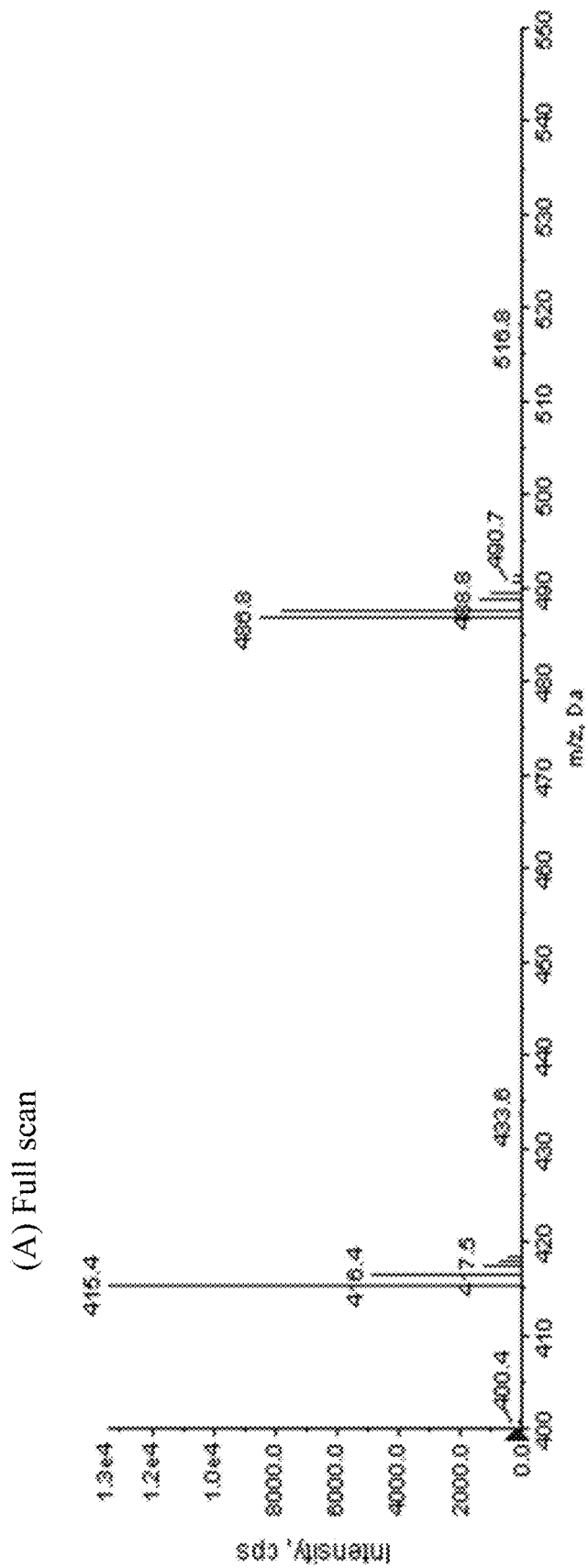
Figure 4a. Mass spectrometric analysis of AZD5104: Full-scan spectrum

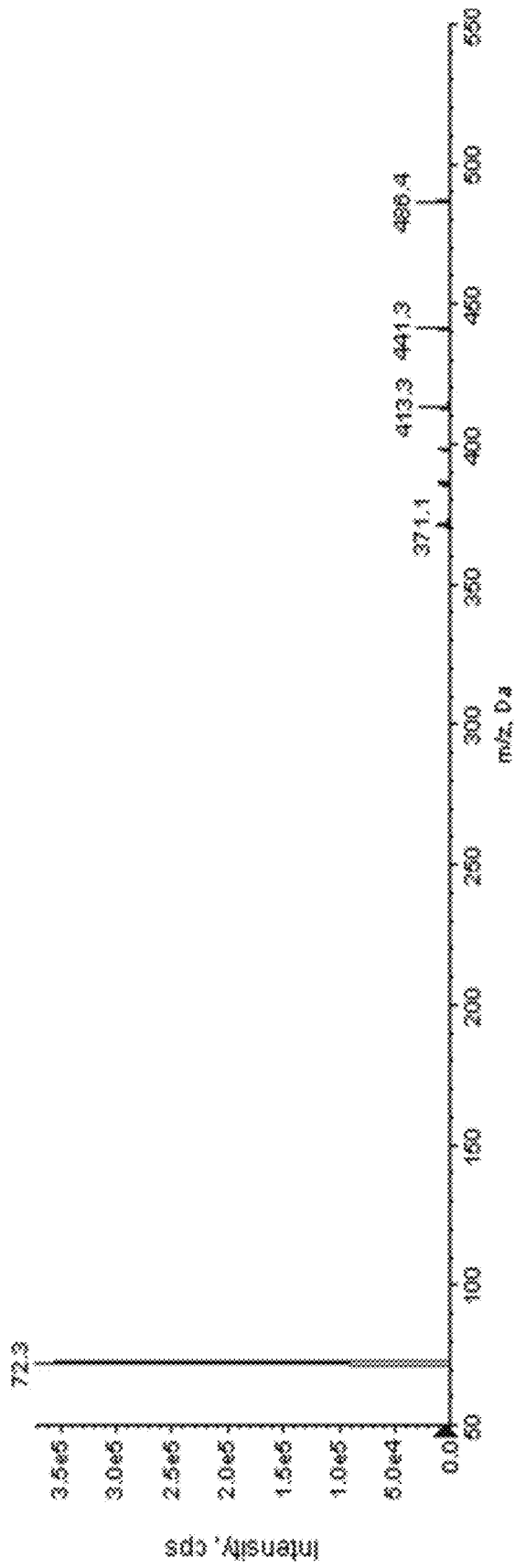
Figure 4b. Mass spectrometric analysis of AZD5104: Product-ion scan spectrum
(B) Product ion scan of protonated molecular ion (*m/z* 486.4)

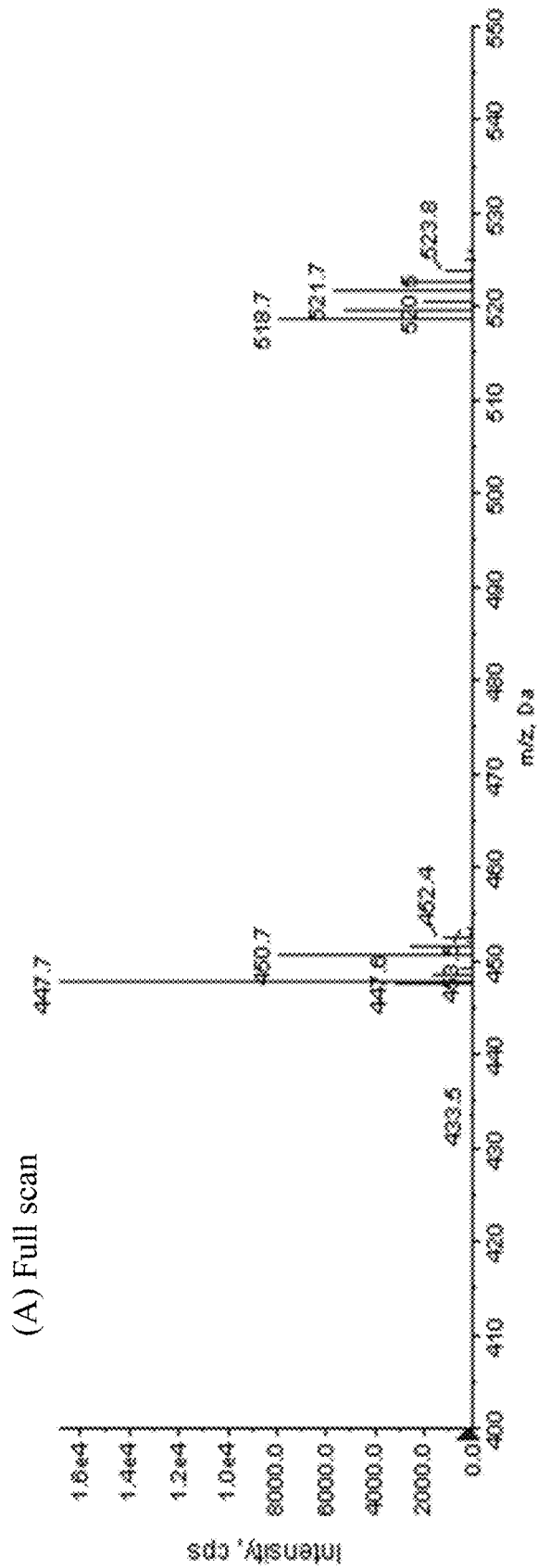
Figure 5a. Mass spectrometric analysis of F1-osimertinib: Full-scan spectrum

Figure 5b. Mass spectrometric analysis of F1-osimertinib: Product-ion scan spectrum
(B) Product ion scan of protonated molecular ion (*m/z* 518.3)
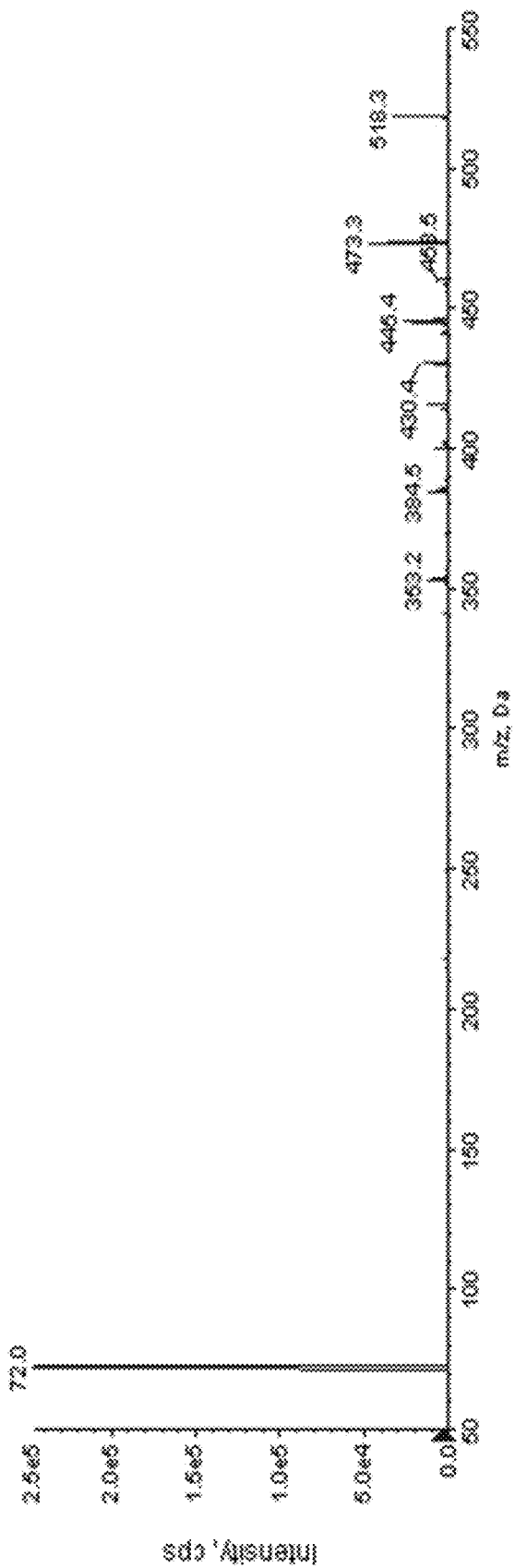

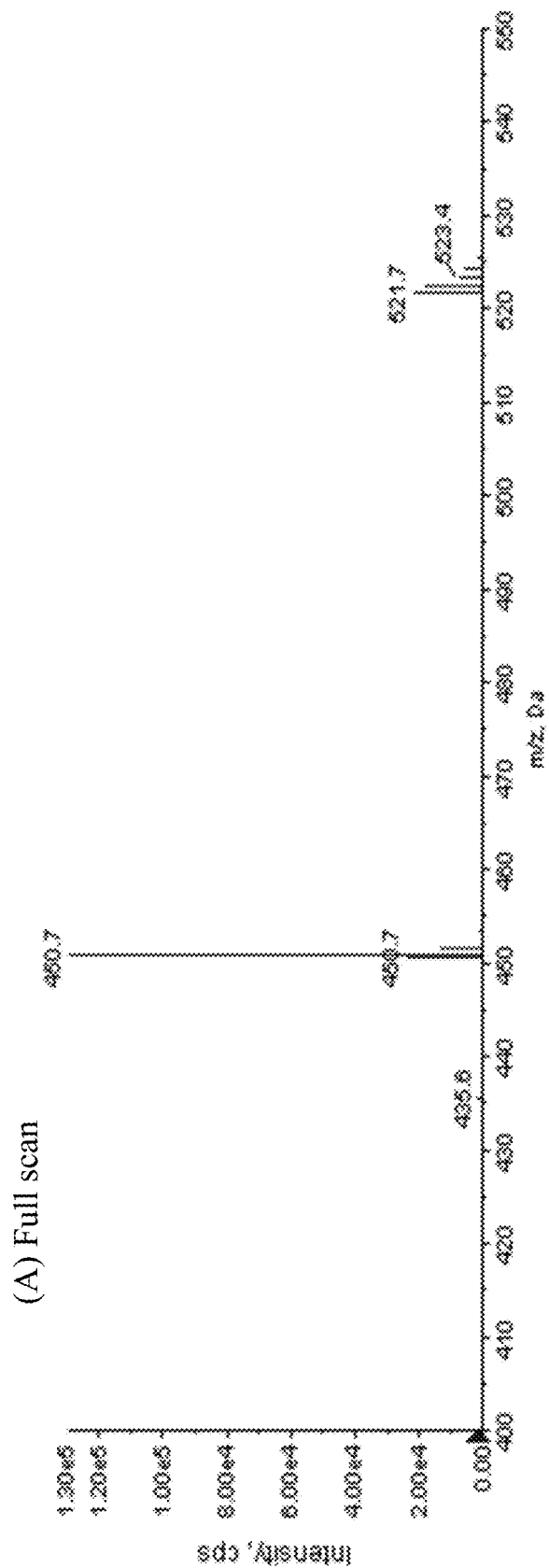
Figure 6a. Mass spectrometric analysis of F1-D3-osimertinib: Full-scan spectrum
(A) Full scan

Figure 6b. Mass spectrometric analysis of F1-D3-osimertinib: Product-ion scan spectrum
(B) Product ion scan of protonated molecular ion (*m/z* 521.3)
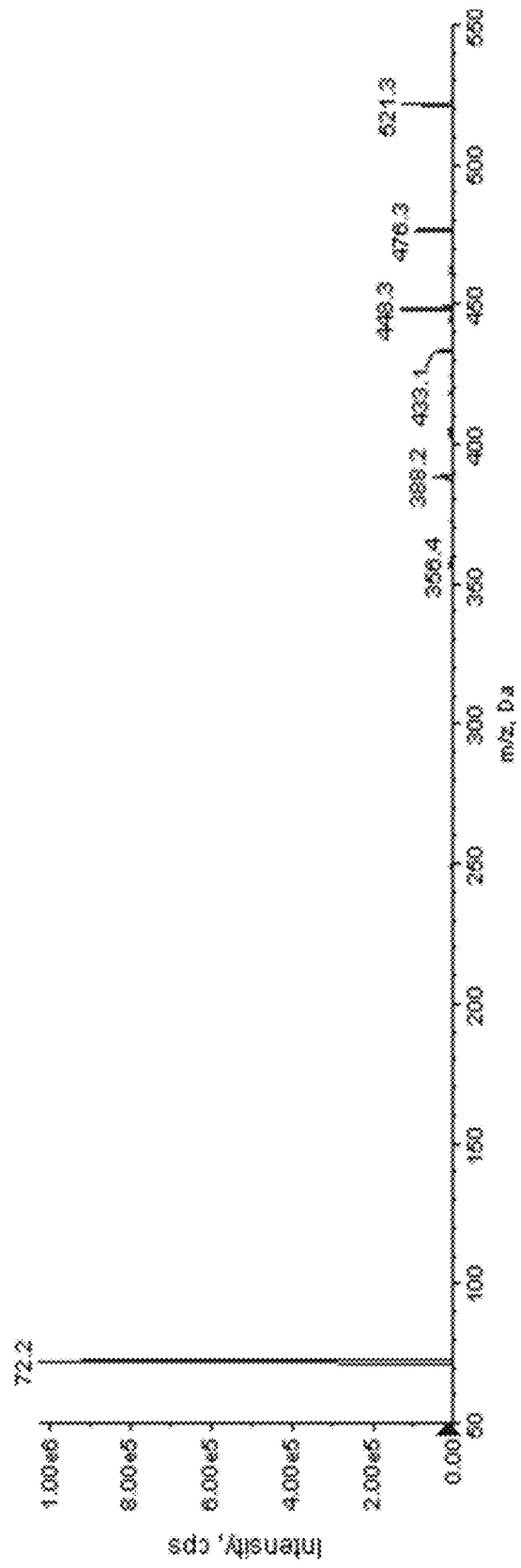

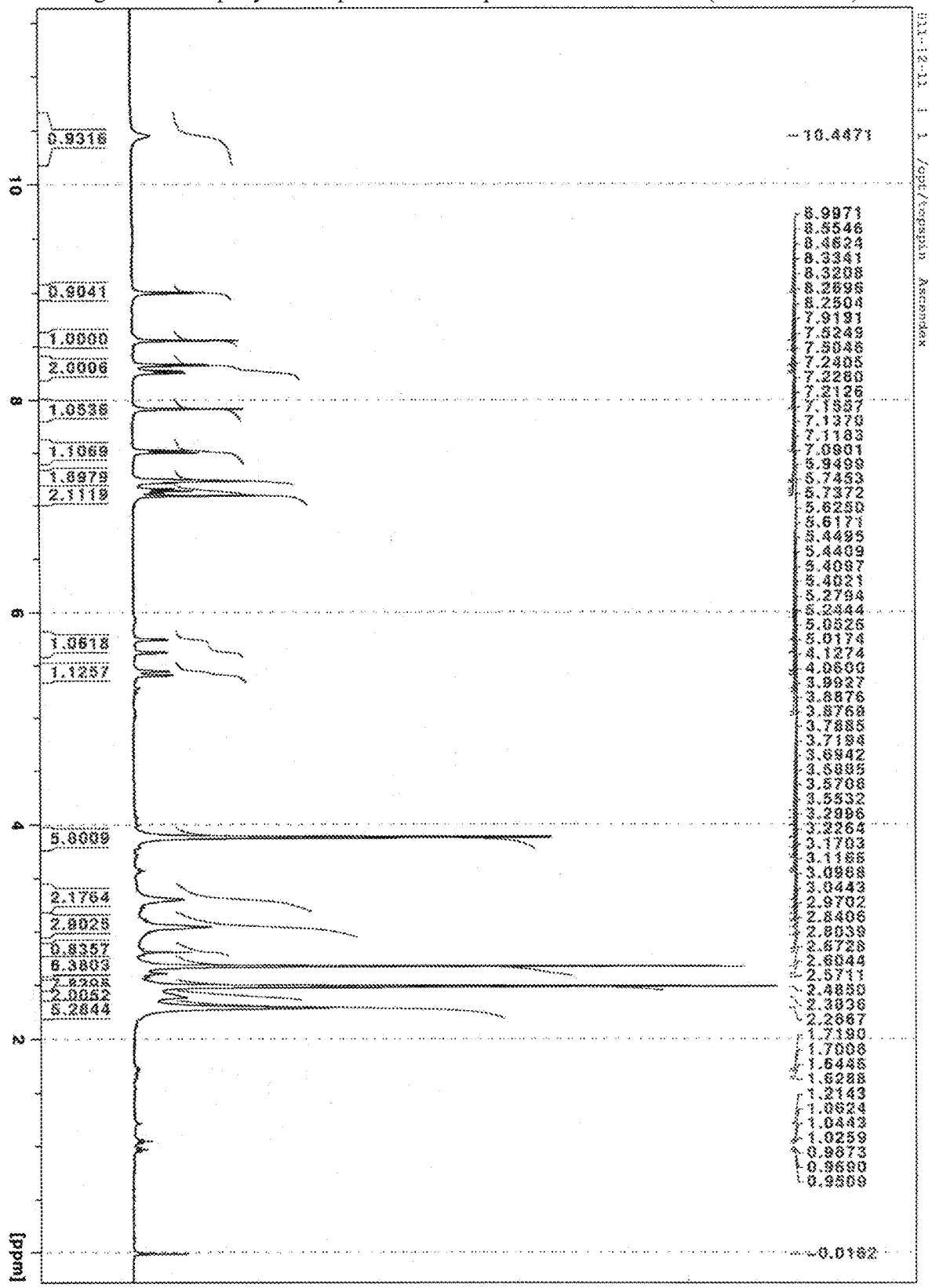
Figure 7. Exemplary NMR spectrum of compounds in the invention (F1-osimertinib).

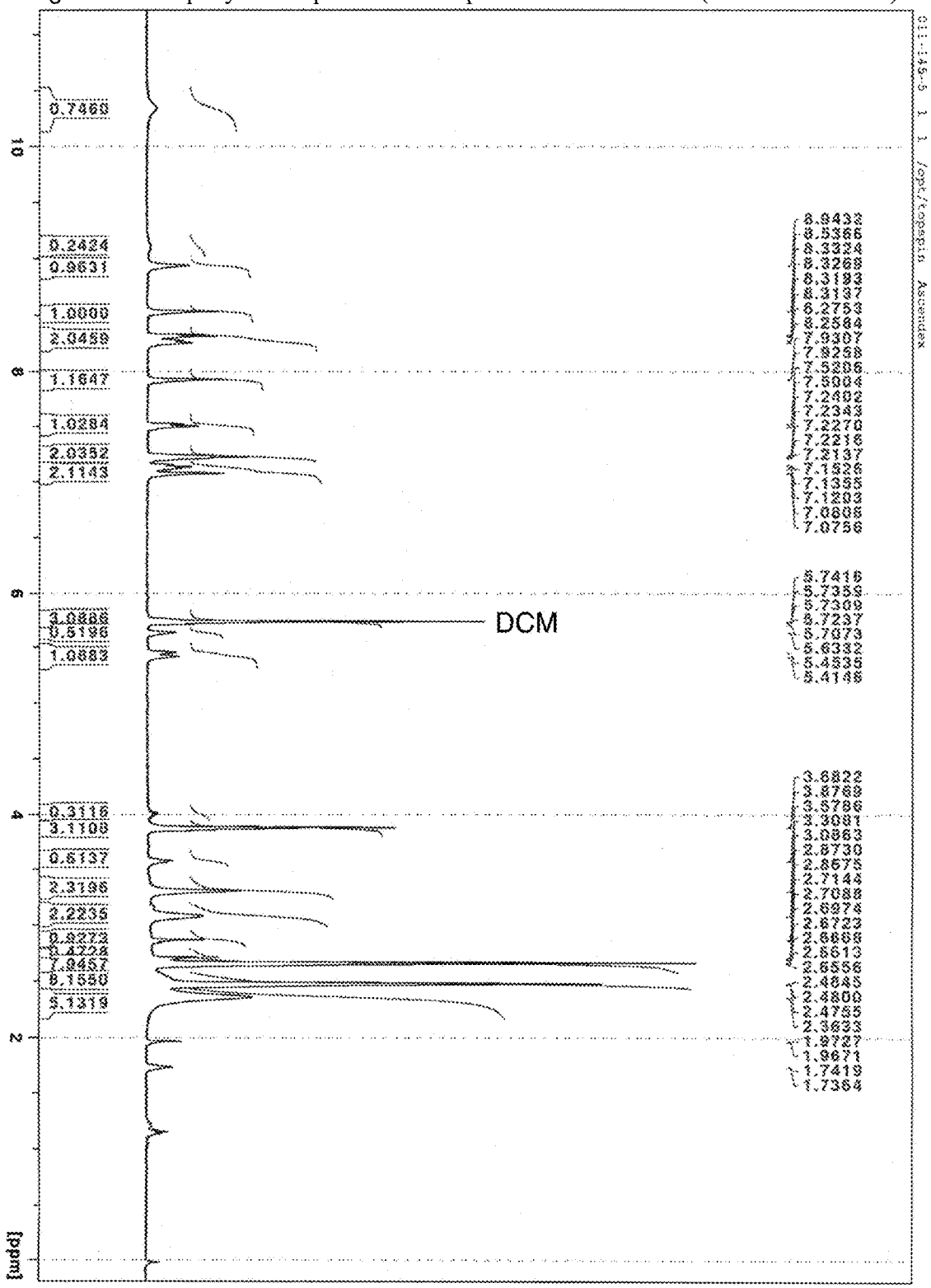
Figure 8. Exemplary NMR spectrum of compounds in the invention (F1-D3-osimertinib).

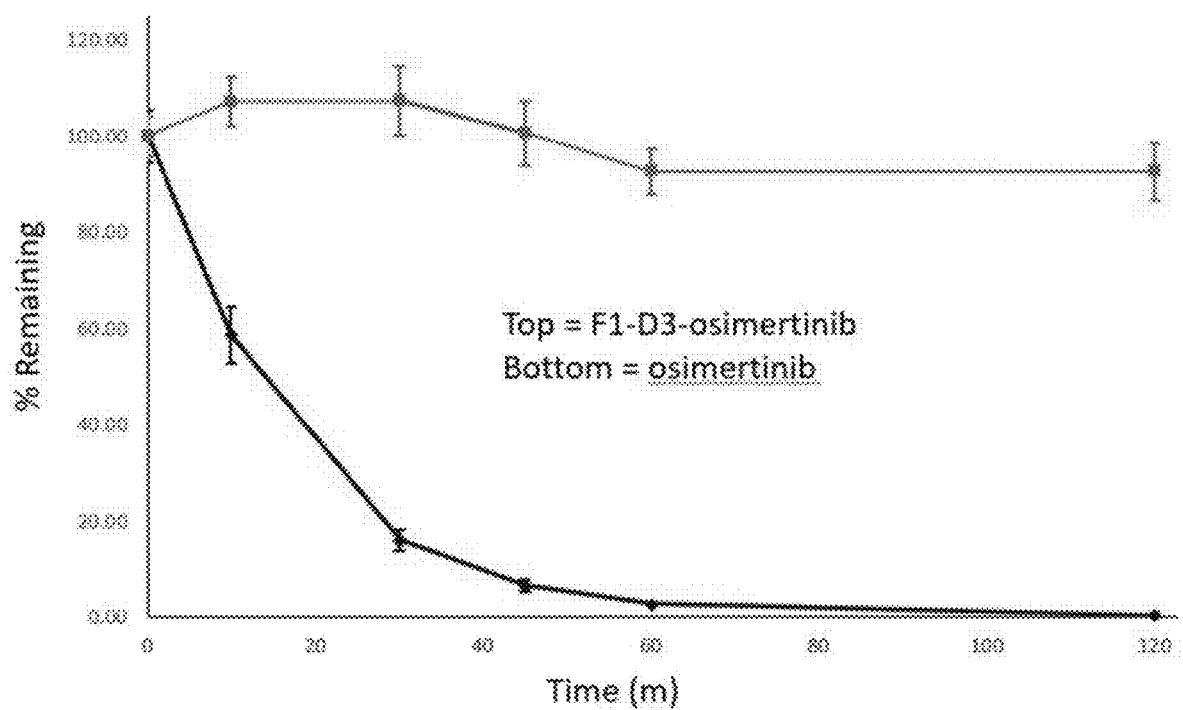
Figure 9. Exemplary results of osimertinib vs. compounds in the invention when co-incubated in human plasma

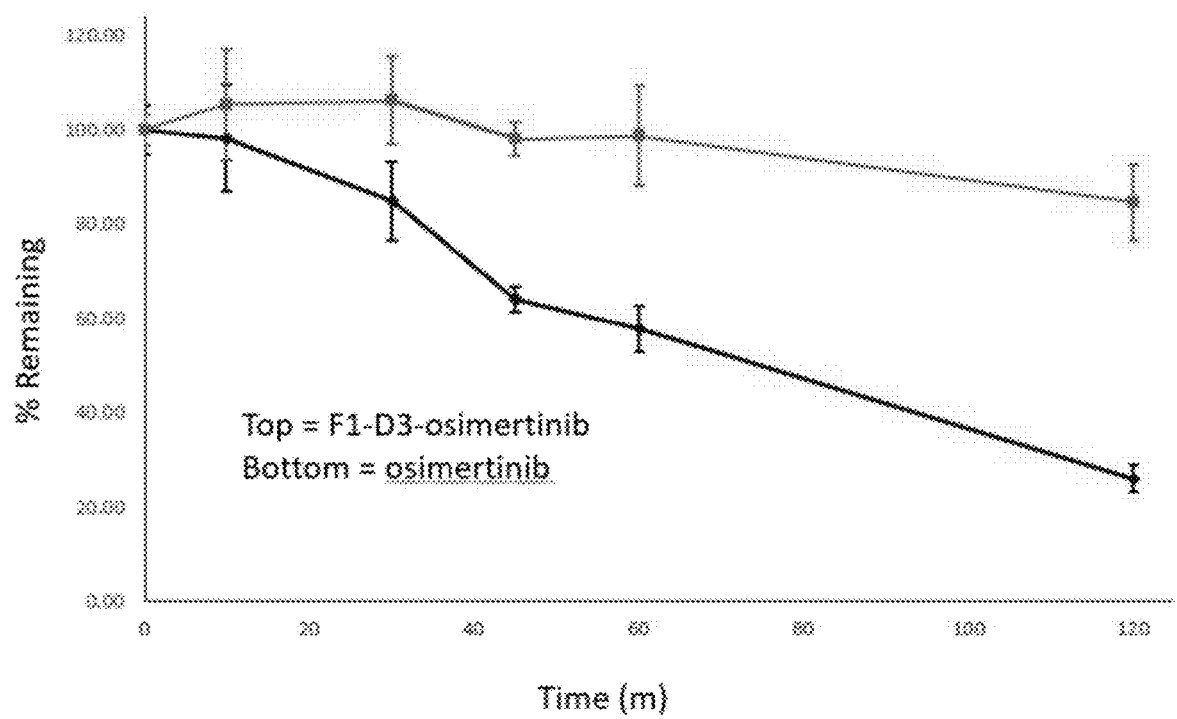
Figure 10. Exemplary results of osimertinib vs. compounds in the invention when co-incubated in rat plasma Figure 11. Exemplary results of osimertinib vs. compounds in the invention when co-incubated in dog plasma
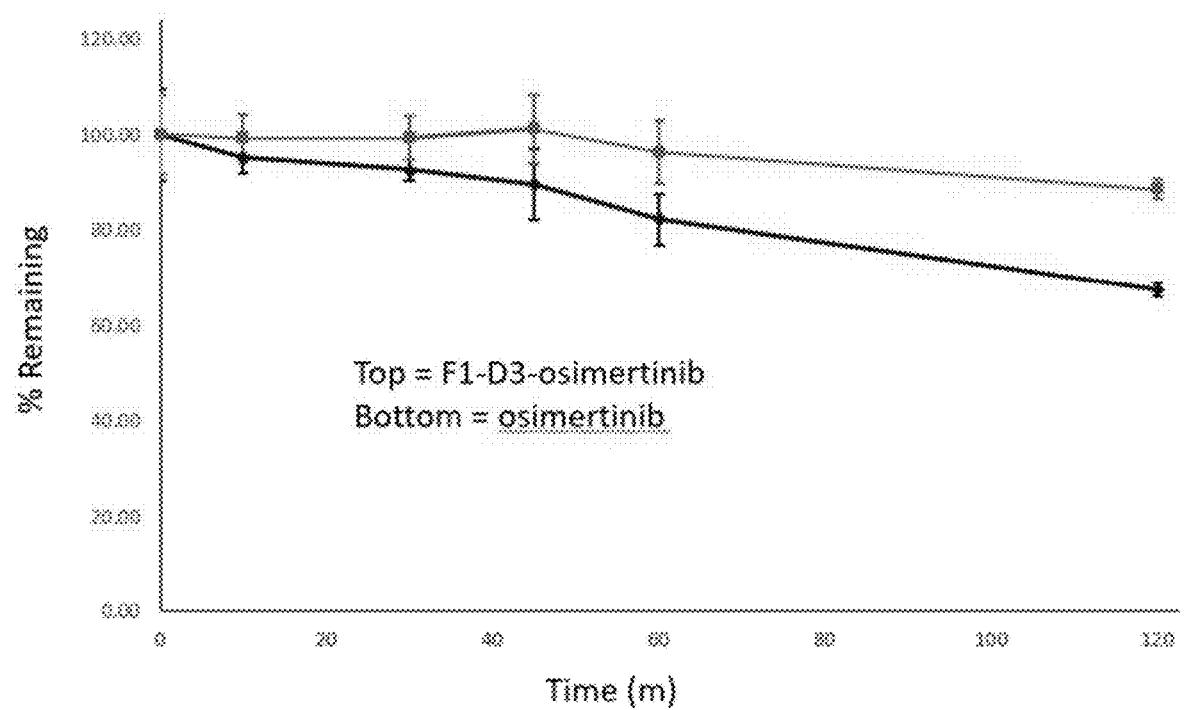

Figure 12. Exemplary results of osimertinib vs. compounds in the invention when co-incubated in mouse plasma
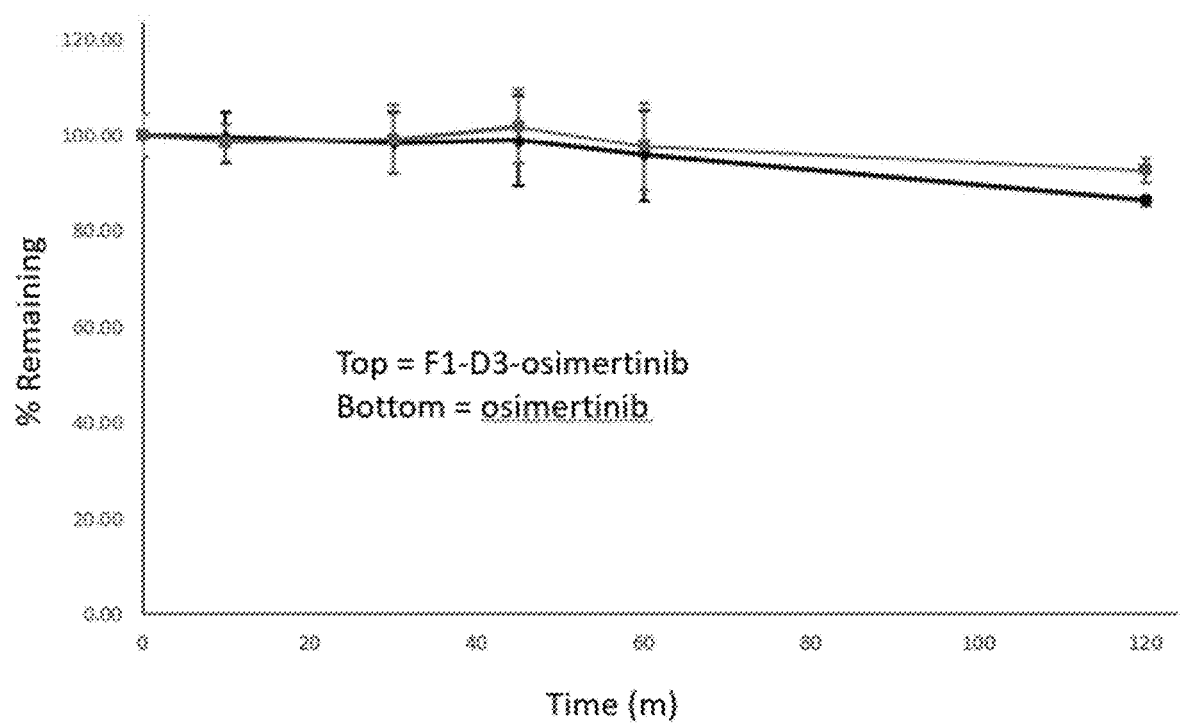

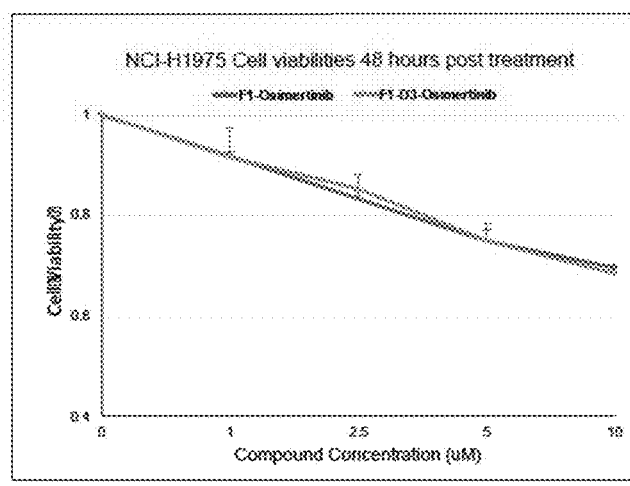
Figure 13. Exemplary results of F1- and F1-D3-Osimertinib on cell viabilities of NCI-H1975 NSCLC carrying activating EGFR T790M mutation

FLUORINE- AND/OR DEUTERIUM-CONTAINING COMPOUNDS FOR TREATING NON-SMALL CELL LUNG CANCER AND RELATED DISEASES

TECHNICAL FIELD

The invention generally relates to novel chemical compounds generated by structural modifications to an existing drug, osimertinib, via fluorination and/or deuteration, and pharmaceutical compositions and methods of preparation and use thereof. These compounds are biologically potent and physiologically active with improved pharmacokinetic, therapeutic, and toxicological profiles over osimertinib for the treatment of various types of cancer, e.g., non-small cell lung cancer (NSCLC), or related diseases and conditions.

BACKGROUND OF INVENTION

Tyrosine kinase inhibitor (TKIs) are used in cancer treatment because they are orally active, highly potent, and have good profile with respect to adverse reactions. Epidermal growth factor receptor (EGFR) is a cell surface transmembrane protein that belongs to a family of receptor tyrosine kinases. Binding by its specific ligand epidermal growth factor (EGF) will activate EGFR intrinsic protein-tyrosine kinase activity to initiate the EGFR signaling cascade. EGFR signaling is critical to normal embryogenesis, cell cycle progression, organ development and human physiology. Aberrant EGFR signaling has been associated with various diseases including cancers. EGFR functional domain mutations leading to increased EGFR activities have been recognized as oncogenic drivers and found in cancers such as non-small-cell lung cancer, metastatic colorectal cancer, gluoblastoma, head and neck cancer, pancreatic cancer and breast cancer. Therefore, targeting EGFR activities has been a major focus in cancer therapy.

NSCLC is the most common type of lung cancer, making up 85% of all lung cancers. It is the leading cause of cancer-related death worldwide, with a 5-year predicted survival rate of 16%. NSCLC can be divided into three subtypes based on their pathological characteristics: adenocarcinoma (ADC, 40%), squamous cell carcinoma (SCC, 30%), and large cell carcinoma (LCC, 15%).

Recent advances in next generation sequencing (NGS) and high-throughput genomic profiling of tumors from NSCLC patients have uncovered over twelve oncogenic drivers, further defining NSCLC as a group of distinct diseases with genetic and cellular heterogeneity. Those oncogenic drivers have become potential therapeutic targets. The development of precision molecular target agents has radically changed the therapeutic landscape for treating NSCLC. Mutations in Kras, BRAF and EGFR were most prominent in patients with adenocarcinoma. EGFR mutations occur in about 30% to 40% ADC in Asian patients and in about 15% in Western patients. First generation EGFR tyrosine kinase inhibitors, such as gefitinib and erlotinib have been used in treatment of EGFR-mutated advanced NSCLC patients with L858R/Del19 and have achieved higher objective response rate, longer progression-free survival and better tolerability, and therefore represent the best therapeutic option in first-line, second-line and maintenance setting for EGFR mutant patients. Unfortunately, virtually all patients develop acquired resistance after nine- to twelve-month treatment, despite an initial benefit. The molecular mechanisms responsible for acquired resistance have been attributed to the up-regulation of the downstream signal by mesenchymal-epidermal transition (MET) amplification and the emergence of recurrent secondary T790M EGFR gatekeeper mutation (60%). Osimertinib (AZD9291) was designed to irreversibly inhibit EGFR-T790M kinase activity, and was developed as an orally active, second-line therapy for patients who develop EGFR-T790M resistant mutation after treatment with first-line EGFR TKIs.

However, over 20% patients treated with Osimertinib will develop adverse reactions, including severe drug-induced toxicities such as high fever, pneumonia and hepatotoxicity. There is an urgent and unmet medical need for innovative cancer therapeutics and treatment methods that can overcome acquired resistance, leading to improved clinical effectiveness with reduced side effects. To this end, structural modification of existing drugs has been playing a significant role in generating new chemical entities that are biologically potent and physiologically active with improved pharmacokinetic, therapeutic, and toxicological profiles.

One such methodology is by fluorine substitution. Over the last twenty years, many fluorinated compounds have been synthesized routinely in pharmaceutical research for generating new drug candidates, including anti-cancer agents. (Shah, et al. 2007 *Journal of Enzyme Inhibition and Medicinal Chemistry* 22(5):527-40.) The size of a fluorine atom (1.4 Å) is comparable to that of a hydrogen atom (1.20 Å), making it possible for the former to replace the latter at a strategically important position. The advantages of a fluorine-substituted compound include higher electron-withdrawing property, greater C—F bond stability over C—H bond, superior lipophilicity, etc. Therefore, fluorination may improve a drug's metabolic stability alter its physicochemical properties, increase its protein-binding affinity, etc.

Another such methodology is to use deuteration as a tool for the optimization of metabolic stability and/or toxicity of drugs. (Suldminder and Monika 2017 *Glob J Pharmaceu Sci.* 1(4): 555566). A primary kinetic isotope effect may be found when a bond to the isotopically labeled atom is being formed or broken. Thus, a demented drug may have a longer half-life than the hydrogen version. This could result in a lower dosage and thus a safer treatment.

BRIEF SUMMARY OF INVENTION

The invention generally relates to novel chemical compounds generated by structural modifications to an existing drug, osimertinib, via fluorination and/or deuteration. These compounds are biologically potent and physiologically active with improved pharmacokinetic, therapeutic, and toxicological profiles over osimertinib, N-(2-{2-dimethylaminoethyl-methylamino}-4-methoxy-5-{[4-(1-methylindol-3-yl)pyrimidin-2-yl]amino}phenyl)prop-2-enamide. The chemical structure of osimertinib is shown below and the mass spectrometric spectra are shown in FIG. 1a and 1b.

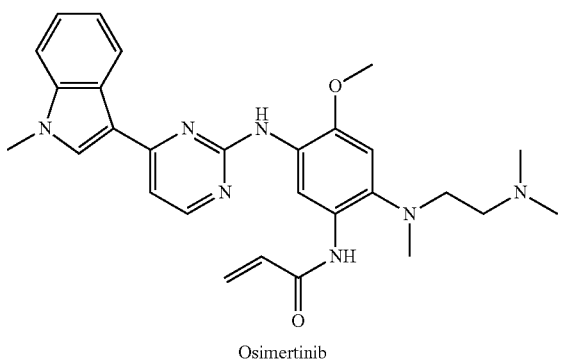

Osimertinib

The compounds disclosed herein are modified versions of osimertinib, wherein one or more hydrogen atoms is substituted with a fluorine atom and/or a deuterium atom at strategic locations. These compounds are epidermal growth factor receptor tyrosine kinase inhibitors (EGFR-TKIs) and are useful for treating various types of cancer, e.g., non-small cell lung cancer, or related diseases and conditions. The inventive compounds of the present invention are represented by the following Formula (I):

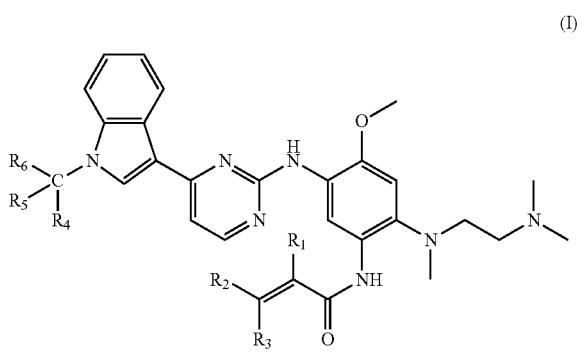

wherein each of $R_1$, $R_2$, $R_3$, $R_4$, $R_5$ and $R_6$ is independently selected from H, D or F, and at least one of $R_1$, $R_2$, $R_3$, $R_4$, $R_5$ and $R_6$ is F.

In another aspect, the invention generally relates to a pharmaceutical composition comprising a compound of the Formula (I) or a pharmaceutically acceptable salt or ester thereof, effective to treat cancer or a related disease or disorder.

In another aspect, the invention generally relates to a dosage form comprising a compound of the Formula (I), wherein the dosage form is suitable for administrating to a subject, animal or human, that suffers from cancer or a related disease or disorder.

In another aspect, the invention generally relates to a method of producing or using a compound of the Formula (I).

The foregoing has outlined rather broadly the features and technical advantages of the invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description. It is to be expressly understood, however, that any description, figure, example, etc. is provided for the purpose of illustration and description only and is by no means intended to define the limits of the invention.

BRIEF DESCRIPTION OF THE DRAWINGS

FIG. 1a. Mass spectrometric analysis of osimertinib: Full-scan spectrum.
FIG. 1b. Mass spectrometric analysis of osimertinib: Product-ion scan spectrum.
FIG. 2. Chemical structures of the first-generation EGFI TKIs.
FIG. 3. Chemical structures of the second-generation EGFI TKIs.
FIG. 4a. Mass spectrometric analysis of AZD5104: Full-scan spectrum.
FIG. 4b. Mass spectrometric analysis of AZD5104: Product-ion scan spectrum.
FIG. 5a. Mass spectrometric analysis of F1-osimertinib: Full-scan spectrum.
FIG. 5b. Mass spectrometric analysis of F1-osimertinib: Product-ion scan spectrum.
FIG. 6a. Mass spectrometric analysis of F1-D3-osimertinib: Full-scan spectrum.
FIG. 6b. Mass spectrometric analysis of F1-D3-osimertinib: Product-ion scan spectrum.
FIG. 7. Exemplary NMR spectrum of compounds, in the invention (F1-osimertinib).
FIG. 8. Exemplary NMR spectrum of compounds in the invention (F1-D3-osimertinib).
FIG. 9. Exemplary results of osimertinib vs. compounds in the invention when co-incubated in human plasma.
FIG. 10. Exemplary results of osimertinib vs. compounds in the invention when co-incubated in rat plasma.
FIG. 11. Exemplary results of osimertinib vs. compounds in the invention when co-incubated in dog plasma.
FIG. 12. Exemplary results of osimertinib vs. compounds in the invention when co-incubated in mouse plasma.
FIG. 13. Exemplary results of F1-osimertinib on cell viabilities of NCI-H1975 NSCLC cells carrying activating EGFR T790M mutation.

DETAILED DESCRIPTION OF THE INVENTION

I. Definitions

Unless otherwise noted, technical tennis are used according to conventional usage.

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g. having the same function or result). In some instances, the term "about" may include numerical values that are rounded to the nearest significant figure.

The term "subject" refers to any animal (e.g., a mammal), including non-human primates, rodents, and the like, which is to be the recipient of a particular treatment. Typically, the terms "subject" and "patient" are used interchangeably herein in reference to a human subject.

The term "effective" as used in connection with an amount of an active agent, refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the patient.

The terms "treating, reducing, or preventing" a condition refer to ameliorating such a condition before or after it has occurred. As compared with an equivalent untreated control, such reduction or degree of prevention is at least 5%, 10%, 20%, 40%, 50%, 60%, 80%, 90%, 95%, or 100% as measured by any standard technique.

The term "pharmaceutically acceptable excipient, carrier, or diluent", as used herein, refers to a pharmaceutically acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; dextrin and cyclodextrin (alpha, beta and gamma); powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free crater; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate, magnesium stearate, and polyethylene oxide-polypropylene oxide copolymer as well as coloring agents, release agents, coating agents, sweetening, flavoring and perfuming agents, preservatives and antioxidants can also be present in the compositions.

II. The Present Invention

The invention provides novel chemical compounds that may be used to, treat cancer (e.g., NSCLC). These compounds are biochemically potent and physiologically active with improved pharmacokinetic, therapeutic and toxicological properties over osimertinib.

The compounds disclosed herein are fluorine- and/or deuterium-substituted versions of osimertinib, where one or more hydrogen atoms are substituted with fluorine and/or deuterium at strategic locations of the molecule. Such strategic fluorine and/or deuterium substitution leads to positive impact on the pharmacokinetic, therapeutic and toxicological profiles of select compounds. The compounds disclosed herein are irreversible EGFR-TKIs. The substitution locations are selected with the specific objective to impact pharmacokinetic, therapeutic, and toxicological properties of the molecule. The resulting compounds have 1 to 6 fluorine with or without additional deuterium substitutions and exhibit more desirable profiles in terms of safety, efficacy and tolerability in the treatment of NSCLC and other related diseases.

First-generation reversible TKIs (e.g., erlotinib, gefitinib and icotinib as shown in FIG. 2) have been reported to be most effective in advanced NSCLC patients whose tumors harbor recurrent somatic activating mutations (EGFRm+). Patients with EGFRm+ tumors normally show good initial responses to the first generation TKIs. Most patients who respond to therapy, however, eventually acquire disease progression in about a year (~9 to 14 months) of treatment. Side effects have also been identified with the use of first generation TKIs, including skin rash and diarrhea reportedly due to the inhibition of wild-type EGFR in skin and gastrointestinal organs. (Pao, et al. 2010 *Nature Reviews Cancer* 10:760-74; Maemondo, et al. 2010 *The New England Journal of Medicine* 362:2380-8; Mitsudomi, et al. 2009 *The Lancet Oncology* 11:121-8; Mok, et 2009 *The New England Journal Medicine* 361:947-57; Rosell, et al. 2012 *The Lancet Oncology;* 13:239-46; Zhou, et al. 2011 *The Lancet Oncology* 12:735-42; Burtness, et al. 2009 *JNCCN* Vol. 7. Suppl. 1, p. 85-21.quiz S2-4.)

Acquisition of a second mutation in EGFR (T790M) is the most common resistance mechanism that is detected in more than 50% of patients after disease progression. The T790M mutation is believed to cause the receptor refractory to inhibition by the first generation EGFR TKIs through exerting effects on both steric hindrance and increased ATP affinity. (Kobayashi, et al. 2005 *New England Journal of Medicine* 352:786-92; Pao, et al. 2005 *PLoS Medicine* 2:e73; Sos, et al. 2010 *Cancer Research* 70:868-74; Yun, et al. 2008 *Proceedings of the National Academy of Sciences USA.;* 105:2070-5.)

Second generation irreversible EGFR TKIs (e.g., neratinib, afatinib and dacomitini) as shown in FIG. 3) are effective in untreated EGFR mutant lung cancer. They have failed, however, to effectively address T790M-mediated resistance. This is in part because of their dose-limiting toxicity connected to the non-selective inhibition of wild-type EGFR. (Li, et al. 2008 *Oncogene* 27:4702-11; Engelman, et al. 2007 *Cancer Research* 67:11924-32; Ranialingani, et al. 2012 *J Clin Oncol* 30:3337-44; Sequist, et al. 2013 *J Clin Oncol* 31:3327-3334; Miller, et al. 2012 *The Lancet Oncology* 13:528-38; Katakami, et al. 2013 *J Gin Oncol* 31:3335-3341; Esker's, et al. 2008 *British Journal of Cancer* 98:80-5.)

Therefore, targeted therapeutics against acquired resistance are quite limited. A significant unmet medical need exists for EGFR TKIs that can effectively target T790M tumors with little or no activity towards wild-type EGFR. To this end, Astra Zeneca has development a third-generation of EGFR TKI for the treatment of non-small cell lung cancer, osimertinib.

Although osimertinib has been shown to be potent against mutants, one of its metabolite (AZD5104) shows a similar affinity towards wild-type EGFR. AZD5104 is formed by N-demethylation (−14 units). FIGS. 4a and 4b shows the mass spectrometric spectra. The formation of AZD5104 gives rise to a toxic metabolite and causes serious side effects during treatment. Deuteration of the N-methyl group is expected to reduce formation of AZD5104 and thus to generate a better safety profile for osimertinib.

Compared to osimertinib, the compounds disclosed herein are potent, selective and irreversible (covalent) inhibitors of both EGFR sensitizing and T790M resistance mutations with much less activity towards wild-type EGFR. Compounds of the invention inhibit phosphorylation of mutant-EGFR much more potently than against wild-type EGFR. Compounds of the invention are also better tolerated and give rise to lesser side effects because of the high selectivity and much reduced activity towards Wild-type EGFR. Exemplary analytical results of mass spectrometric analyses are shown in FIGS. 5a and 5b and in FIGS. 6a and 6b, and those from NMR analysis in FIGS. 7 and 8.

In addition to use as a third-line therapy, compounds of the invention may also be used to treat EGFRm+ TKI-naïve patients by targeting both sensitizing and T790M tumor cell populations that co-exist in a proportion of tumors. This approach may lead to delayed disease progression and improved survival rate.

In the present invention, all compounds disclosed herein have the general structure of Formula (I):

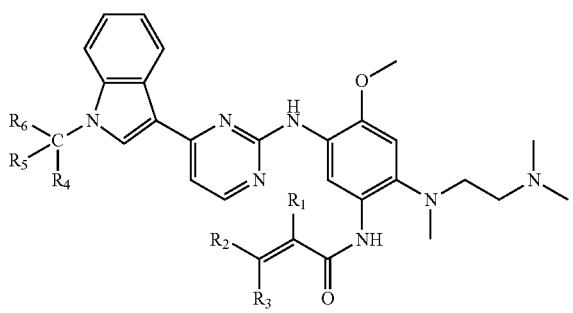

(I)

wherein each of $R_1$, $R_2$, $R_3$, $R_4$, $R_5$ and $R_6$ is independently selected from H, D or F, and at least one of $R_1$, $R_2$, $R_3$, $R_4$, $R_5$ and $R_6$ is F.

In another aspect, the invention relates to a pharmaceutical composition comprising a compound of the Formula (I), or a pharmaceutically acceptable salt or ester thereof, effective to treat cancer or a related disease or disorder.

In another aspect, the invention relates to a dosage form comprising a compound of the Formula (I), wherein the dosage form is suitable for administrating to a subject, animal or human, that suffers from cancer or a related disease or disorder.

In another aspect, the invention relates to a method of making or using a compound of the Formula (I).

In certain embodiments, each of $R_1$ in the compound is F and each of $R_2$, $R_3$, $R_4$, $R_5$ and $R_6$ is H, having the structural Formula (II):

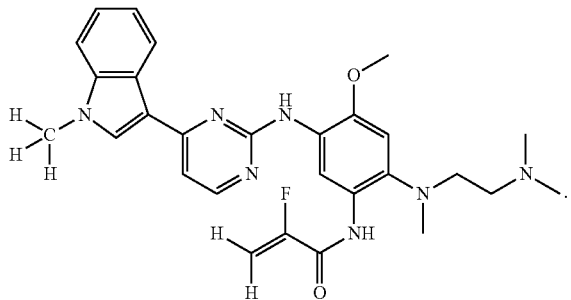

(II)

In another aspect, the invention relates to a pharmaceutical composition comprising a compound of the Formula (II), or a pharmaceutically acceptable salt or ester thereof, effective to treat cancer or a related disease or disorder.

In another aspect, the invention relates to a dosage form comprising a compound of the Formula (II), wherein the dosage form is suitable for administrating to a subject, animal or human, that suffers from cancer or a related disease or disorder.

In another aspect, the invention relates to a method of producing or using a compound of the Formula (II).

In certain embodiments, each of $R_2$ and $R_3$ in the compound is F and each of $R_1$, $R_4$, $R_5$ and $R_6$ is H, having the structural Formula (III):

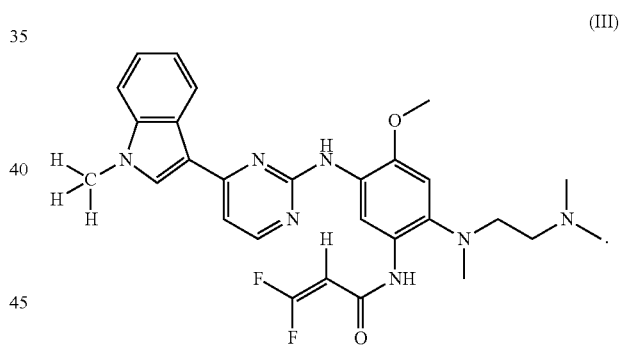

(III)

In another aspect, the invention relates to a pharmaceutical composition comprising a compound of the Formula (IR or a pharmaceutically acceptable salt or ester thereof, effective to treat cancer or a related disease or disorder.

In another aspect, the invention relates to a dosage form comprising a compound of the Formula (III), wherein the dosage form is suitable for administrating to a subject, animal or human, that suffers from cancer or a related disease or disorder.

In another aspect, the invention relates to a method of producing or using a compound having the structure of Formula (III).

In certain embodiments, each of $R_1$, $R_2$ and $R_3$ in the compound is F, and each of $R_4$, $R_5$ and $R_6$ is H, having the structural formula (IV):

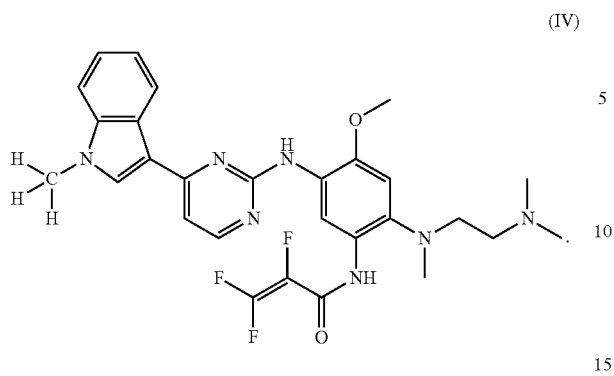

(IV)

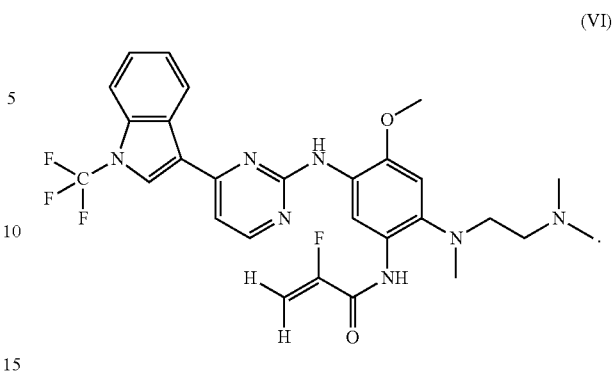

(VI)

In another aspect, the invention relates to a pharmaceutical composition comprising a compound of the Formula (IV), or, a pharmaceutically acceptable salt or ester thereof effective to treat cancer or a related disease or disorder.

In another aspect, the invention relates to a dosage form comprising a compound of the Formula (IV), wherein the dosage form is suitable for administrating to a subject, animal or human, that suffers from cancer or a related disease or disorder.

In another aspect, the invention relates to a method of producing or using a compound of the Formula (IV).

In certain embodiments, each of $R_1$, $R_2$ and $R_3$ in the compound is H, and each of $R_4$, $R_5$ and $R_6$ is F, having the structural formula (V):

In another aspect, the invention relates to a pharmaceutical composition comprising a compound of the Formula (VI), or a pharmaceutically acceptable salt or ester thereof effective to treat cancer or a related disease or disorder.

In another aspect, the invention relates to a dosage form comprising a compound of the Formula (VI), wherein the dosage form is suitable for administrating to a subject, animal or human, that suffers from cancer or a related disease or disorder.

In another aspect, the invention relates to a method of producing or using a compound of the Formula (VI).

In certain embodiments, each of $R_2$ and $R_3$ in the compound is F, $R_1$ is H, and each of $R_4$, $R_5$ and $R_6$ is F, having the structural formula (VII):

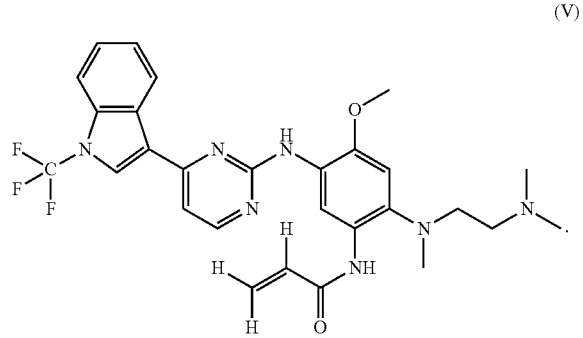 [SMILES: C=CC(=O)Nc1cc(Nc2nccc(-c3cn(C(F)(F)F)c4ccccc34)n2)c(OC)cc1N(C)CCN(C)C]

(V)

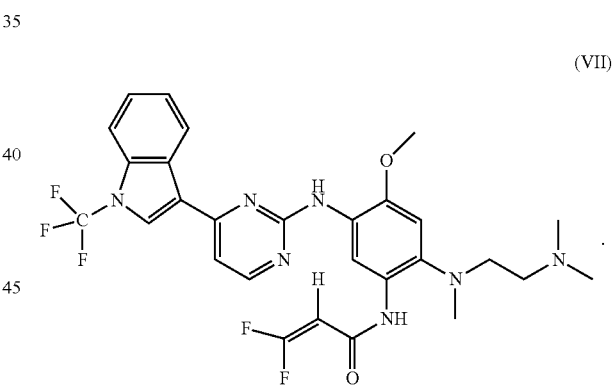

(VII)

In another aspect, the invention relates to a pharmaceutical composition comprising a compound of the Formula (V), or a pharmaceutically acceptable salt or ester thereof, effective to treat cancer or a related disease or disorder.

In another aspect, the invention relates to a dosage form comprising a compound of the Formula (V), wherein the dosage form is suitable for administrating to a subject, animal or human, that suffers from cancer or a related disease or disorder.

In another aspect, the invention relates to a method of producing or using a compound of the Formula (V).

In certain embodiments, each of $R_1$ in the compound is F, each of $R_2$ and $R_3$ is H, and each of $R_4$, $R_5$ and $R_6$ is F, having the structural formula (VI):

In another aspect, the invention relates to a pharmaceutical composition comprising a compound of the Formula (VII), or a pharmaceutically acceptable salt or ester thereof, effective to treat cancer or a related disease or disorder.

In another aspect, the invention relates to a dosage form comprising a compound of the Formula (VII), wherein the dosage form is suitable for administrating to a subject, animal or human, that suffers from cancer or a related disease or disorder.

In another aspect, the invention relates to a method or producing or using a compound of the Formula (VII).

In certain embodiments, each of $R_1$, $R_2$, $R_3$, $R_4$, $R_5$ and $R_6$ in the compound is F, having the structural formula (VIII):

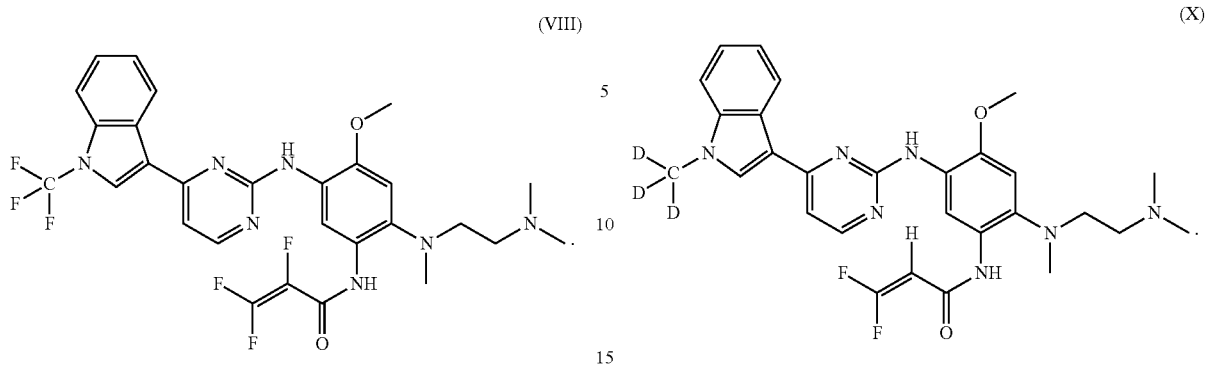

(VIII)

(X)

In another aspect, the invention relates to a pharmaceutical composition comprising a compound of the Formula (VIII), or a pharmaceutically acceptable salt or ester thereof, effective to treat cancer or a related disease or disorder.

In another aspect, the invention relates to a dosage form comprising a compound of the Formula (VIII), wherein the dosage form is suitable for administrating to a subject, animal or human, that suffers from cancer or a related disease or disorder.

In another aspect, the invention relates to a method of producing or using a compound of the Formula (VIII).

In certain embodiments, $R_1$ is F, each of $R_2$ and $R_3$ is H, and each of $R_4$, $R_5$ and $R_6$ in the compound is D, having the structural formula (IX):

In another aspect, the invention relates to a pharmaceutical composition comprising a compound of the Formula (X), or a pharmaceutically acceptable salt or ester thereof, effective to treat cancer or a related disease or disorder.

In another aspect, the invention relates to a dosage form comprising a compound of the Formula (X), wherein the dosage form is suitable for administrating to a subject, animal or human, that suffers from cancer or a related disease or disorder.

In another aspect, the invention relates to a method of producing or using a compound of the Formula (X).

In certain embodiments, each of $R_1$, $R_2$ and $R_3$ is F, and each of $R_4$, $R_5$ and $R_6$ in the compound is D, having the structural formula (XI):

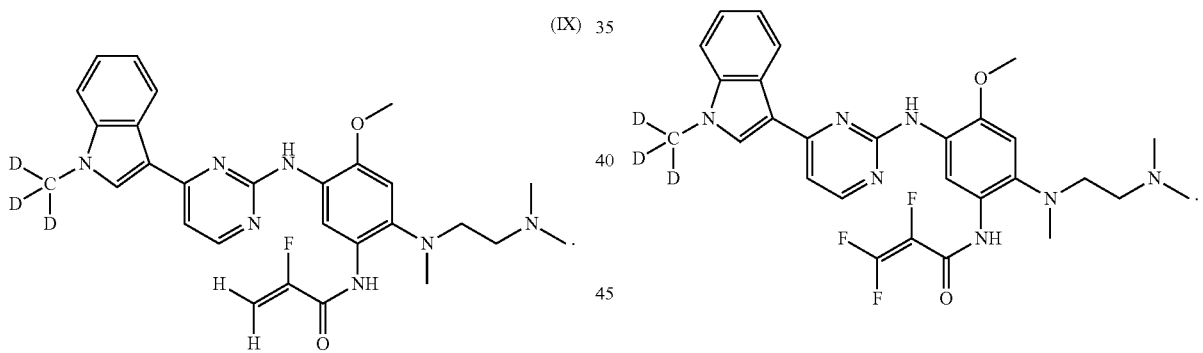

(IX)

(XI)

In another aspect, the invention relates to a pharmaceutical composition comprising a compound of the Formula (IX), or a pharmaceutically acceptable salt or ester thereof, effective to treat cancer or a related disease or disorder.

In another aspect, the invention relates to a dosage form comprising a compound of the Formula (IX), wherein the dosage form is suitable for administrating to a subject, animal or human, that suffers from cancer or a related disease or disorder.

In another aspect, the invention relates to a method of producing or using a compound of the Formula (IX).

In certain embodiments, $R_1$ is H, each of $R_2$ and $R_3$ is F, and each of $R_4$, $R_5$ and $R_6$ in the compound is D, having the structural formula (X):

In another aspect, the invention relates to a pharmaceutical composition comprising a compound of the Formula (XI), or a pharmaceutically acceptable salt or ester thereof, effective to treat cancer or a related disease or disorder.

In another aspect, the invention relates to a dosage form comprising a compound of the Formula (XI), wherein the dosage form is suitable for administrating to a subject, animal or human, that suffers from cancer or a related disease or disorder.

In another aspect, the invention relates to a method of producing or using a compound of the Formula (XI).

In certain embodiments, the compounds of Formulas (I) to (XI) are in the form of a mesylate salt.

In another aspect, the invention relates to a pharmaceutical composition comprising at least one compound selected from the group consisting of the compounds of Formulas (I) to (XI) or a pharmaceutically acceptable salt or ester thereof.

In yet another aspect, the invention relates to a unit dosage form comprising the pharmaceutical composition disclosed herein. The unit dosage is suitable for administration to a subject suffering cancer (e.g., lung cancer, NSCLC) or a related disease and condition.

In yet another aspect, the invention relates to a method for treating, reducing, or preventing a disease or disorder. The method includes: administering to a subject in need thereof a pharmaceutical composition comprising at least one compound selected from the group consisting of the compounds of Formulas (I) to (XI), or a pharmaceutically acceptable salt or ester thereof.

In certain embodiments, the cancer is lung cancer. In certain preferred embodiments, the cancer is non-small cell lung cancer. In certain preferred embodiments, the cancer is non-small cell lung cancer with EGFR T790M mutation.

In certain embodiments, the pharmaceutical composition of the invention is administered as a last line cancer therapeutic. In certain embodiments, the pharmaceutical composition is administered as a second line cancer therapeutic. In certain embodiments, the pharmaceutical composition is administered as a first line cancer therapeutic.

In certain embodiments of the method, the pharmaceutical composition is administered to a subject who is a NSCLC patient with EGFRm+ and EGFR T790M mutation. In certain embodiments, the subject has been previously treated with one or more first generation reversible TKIs. In certain embodiments, the subject has been previously treated with one or more second generation irreversible TKIs. In certain embodiments, the subject has been previously treated with both one or more first generation TKIs and one or more second generation irreversible TKIs.

In certain embodiments, the diseases and conditions that may benefit from treatment using the compounds, pharmaceutical compositions, unit dosage forms and treatment methods disclosed herein include any diseases and disorders that may be addressed by EGFR-TKIs.

In certain preferred embodiments, the method of treatment includes administering to a subject in need thereof a pharmaceutical composition comprising a compound of any of the Formulas (I) to (XI), or a pharmaceutically acceptable salt or ester thereof.

In certain preferred embodiments, one or more other anti-cancer agents may be administered with the inventive compound. The one or more other anti-cancer agents are selected from methotrexate, afatinib dimaleate, alectinib, pemetrexed disodium, bevacizumab, carboplatin, ceritinib, crizotinib, ramucirumab, docetaxel, erlotinib hydrochloride, methotrexate, gefitinib gemcitabine hydrochloride, pembrolizumab, mechlorethamine hydrochloride, vinorelbine tartrate, necitumumab, nivolumab, paclitaxel, and erlotinib hydrochloride.

IV. Examples

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

Example 1

Synthetic Scheme for Compound 10

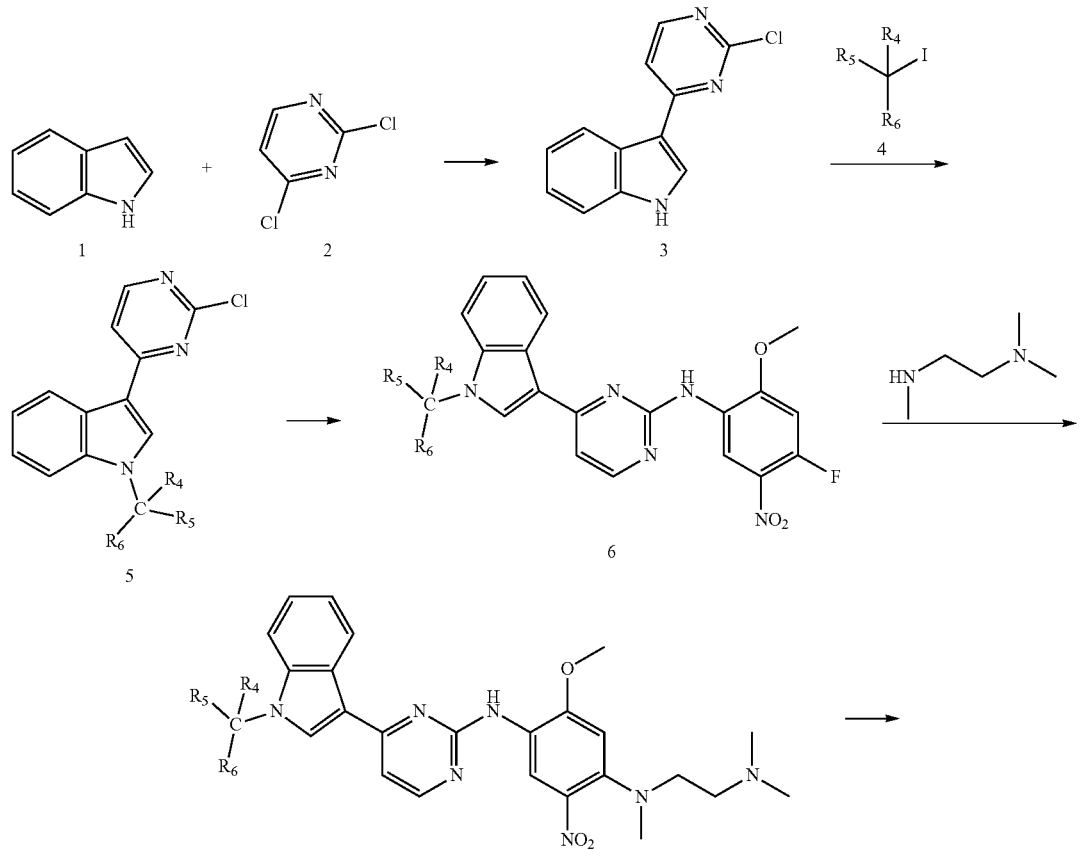

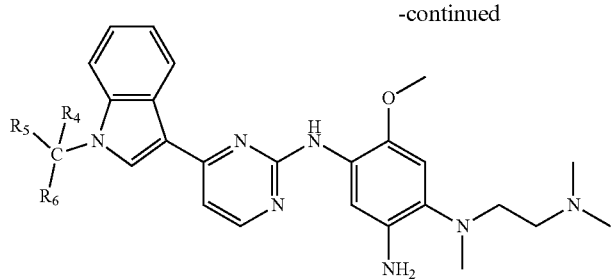
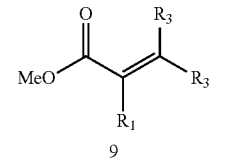
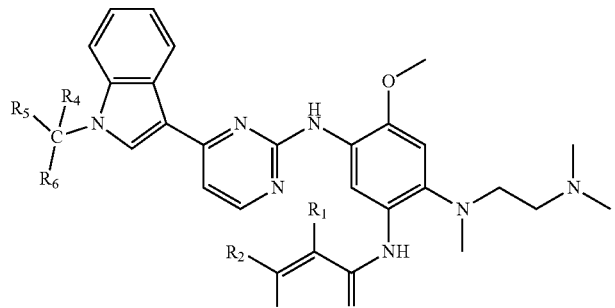

Synthesis of Compound 3

3-(2-Chloropyrimidin-4-yl)-1H-indole (compound 3)

Methylmamesium bromide (3 M in diethyl ether) (100 mL) was added dropwise aver a period of 10 min to a stirred solution of 1H-indole (35.2 g) in THF (500 mL) at 0° C. under nitrogen. The resulting solution was stirred for 60 min. 2,4-Dichloropyrimidine (44.7 g) was added in one portion. The resulting solution was heated at reflux for 5 hours and stirred at ambient temperature for 16 h. The reaction was quenched by the addition of water (400 mL) and EtOAc (500 mL). The organic layer was evaporated to dryness and purified by flash silica chromatography. Pure fractions were evaporated to dryness, 3-(2-chloropyrimidin-4-yl)-1H-indole (compound 3, 19 g) as a yellow solid.

Synthesis of Compound 4

3-(2-Chloropyrimidin-4-yl)-1-methylindole (Compound 4)

Sodium hydride (2.7 g, 60% in mineral oil) was added portionwise to 3-(2-chloropyrimidin-4-yl)-1H-indole (12 g) in THF (250 mL) at 0° C. The resulting mixture was stirred at 0° C. for 30 min before iodomethane (1.3 equiv.) was added. The mixture was stirred at 0° C. for 1 h. The reaction was quenched by the addition of saturated aqueous NaHCO$_3$ solution (400 mL) and EtOAc (400 mL). The organic layer was washed with saturated brine (200 mL). The organic layer was evaporated to afford crude product (compound 4, 9.3 g) as a pale orange solid.

Synthesis of Compound 5

N-(4-Fluoro-2-methoxy-5-nitrophenyl)-4-(1-methylindol-3-yl)-pyrimidin-2-amine (Compound 5)

4-Methylbenzenesulfonic acid hydrate (8.7 g) was added in one portion to 3-(2-chloropyrimidin-4-yl)-1-methylindole (9.3 g) and 4-fluoro-2-methoxy-5-nitroaniline (7.1 g) in n-butanol (200 mL). The resulting mixture was stirred at reflux for 1 h. The mixture was cooled to room temperature. The precipitate was collected by filtration, washed with n-butanol (50 mL), and dried under vacuum to afford N-(4-fluoro-2-methoxy-5-nitrophenyl)-4-(1-methylindol-3-yl)pyrimidin-2-amine as a yellow solid (Compound 5, 15.5 g).

Synthesis of Compound 7

N'-(2-Dimethylaminoethyl)-2-methoxy-N'-methyl-N-[4-(1-methylindol-3-yl)pyrimidin-2-yl]-5-nitrobenzene-1,4-diamine (Compound 7)

Compound 6 (7.7 mL) was added to a suspension of N-(4-fluoro-2-methoxy-5-nitrophenyl)-4-(1-methylindol-3-yl)pyrimidin-2-amine (compound 5, 15.5 g, 0.79) and K2CO3 (16.3 g) DMF (60 mL). The mixture was heated at 60° C. for 60 min and then water (150 mL) was added. Solids were filtered and rinsed with water. The crude dark red product was directly used in the next step without further purification.

Synthesis of Compound 8

N1-(2-Dimethylaminoethyl)-5-methoxy-N1-methyl-N4-[4-(1-methylindol-3-yl)pyrimidin-2-yl]benzene-1,2,4-triamine (Compound 8)

Compound 7 from the previous step, iron (12.8 g), and ammonium chloride (1.42 g) were heated in ethanol (100 mL) and water (30 mL) at reflux for 1.5 h. The mixture was cooled and filtered. The solids were rinsed with DCM. The filtrate was concentrated to approximately 20 mL, and NaOH (1 N, 50 mL) was added. The gray precipitates were filtered off and rinsed with DCM. The mixture was partitioned and the organic layer was washed with NH$_4$OH (50 mL), brine (100 mL) and concentrated to a brown foam (compound 8, 12 g).

Synthesis of Compound 10

2-Fluoroacrylic acid (0.5 g) was added dropwise to a stirred solution of compound 8 (2 g) EDC-HCl (1.28 g) and DIPEA (1.15 g) in DMF (10 mL). The mixture was stirred for 16 hours and then diluted with DCM (50 mL) and washed with brine, NH$_4$OH, brine. The organic layer was concentrated and purified by column chromatography. Pure fractions were evaporated to dryness and triturated with ether to afford compound 10 (0.35 g) as an off-white solid.

The resulting compound 10 has the following forms (a)-(j), wherein each of $R_1$-$R_6$ corresponds with the same in the compound of Formula (I):
In case of compound 10a, R1=F, and R2=R3=R4=R5=R6=H;
In case of compound 10b, R1=H, R2=R3=F, and R4=R5=R6=H;
In case of compound 10c, R1=R2=R3=F, and R4=R5=R6=H;
In case of compound 10d, R1=R2=R3=H, and R4=R5=R6=F;
In case of compound 10e, R1=F, R2=R3=H, and R4=R5=R6=F;
In case of compound 10f, R1=H, and R2=R3=F=R4=R5=R6=F;
In case of compound 10g, R1=R2=R3=R4=R5=R6=F;
In case of compound 10h, R1=F, R2=R3=H, and R4=R5=R6=D;
In case of compound 10i, R1=H, R2=R3=F, and R4=R5=R6=D;
In case of compound 10j, R1=R2=R3=F, and R4=R5=R6=D.

FIG. 7 shows the NMR spectrum of compound 10a (F1-osimertinib). $^1$H-NMR (300 MHz, DMSO-d6) 10.45 (s, 1H), 9.00 (s, 1H), 8.55 (s, 1H), 8.33 (d, 1H), 8.26 (d, 1H), 7.92 (s, 1H), 7.51 (d, 1H), 7.27-7.18 (m, 2H), 7.14 (t, 1H), 7.09 (s, 1H), 5.68 (dd, 1H), 5.43 (dd, 1H), 3.89 (s, 3H), 3.88 (s, 3H), 3.09-3.00 (m, 2H), 2.67 (s, 3H), 2.45-2.35 (m, 2H), 2.29 (s, 6H).

FIG. 8 shows the NMR spectrum of compound 10h (F1-D3-osimertinib). $^1$H-NMR (300 MHz, DMSO-d6): 10.45 (s, 1H), 9.00 (s, 1H), 8.55 (s, 1H), 8.33 (d, 1H), 8.26 (d, 1H), 7.92 (s, 1H), 7.51 (d, 1H), 7.27-7.18 (m, 2H), 7.14 (t, 1H), 7.09 (s, 1H), 5.68 (dd, 1H), 5.43 (dd, 1H), 3.88 (s, 3H), 3.09-3.00 (m, 2H), 2.67 (s, 3H), 2.45-2.35 (m, 2H) 2.29 (s, 6H).

Example 2

Incubation of Osimertinib in Animal and Human Plasma Verses Compounds Described in the Invention Incubation Procedure Briefly, 40 μL of osimertinib was co-incubated with an equal volume of one of the compounds described in this invention at the same concentration in blank plasma (human, beagle dog, Sprague-Dawley rat or CD-1 mouse). The tubes were incubated in a dry bath incubator for six time points ranging from 0 to 120 minutes. At each time point, the plasma was crashed with 200 μL internal standard working solution in acetonitrile, then vortexes and centrifuged. A portion of the supernatant was then transferred to autosampler vials for injection into the LC-MS/MS system.

LC-MS/MS Analysis

Chromatographic retention of osimertinib and the compounds described in the invention was obtained on an ACE 3 C18, 2.1×50 min, 3.0 μm column (Aberdeen, Scotland) under gradient conditions with a flow rate of 0.3 mL/minute. Analytes were detected by multiple reaction monitoring using an MDS Sciex API 4000 mass spectrometer (Applied Biosystems/MDS Sciex, Concord, Ontario, Canada) in positive mode. Data was captured using Analyst®, Version 1.6.2 (Applied Biosystems/MDS Sciex, Foster City, Calif.) and then exported to Excel® (Microsoft, Seattle, Wash.) for further data reduction.

Results from Co-Incubation in Human Plasma

Osimertinib decreased rapidly when incubated in human plasma as shown in FIG. 9. Surprisingly, compounds of the invention remained stable under the same experimental conditions when co-dosed with osimertinib at 1:1 ratio.

Results from Co-Incubation in Rat Plasma

After incubating for two hours in rat plasma, the remaining percentage of osimertinib was around 35% of the initial concentration, see FIG. 10. On the other hand, the remaining percentage compounds of the invention was approximately 95% of their respective initial concentrations, indicating a much improved ex-vivo stability.

Results from Co-Incubation in Dog Plasma

After incubating for two hours in beagle plasma, the remaining percentage of osimertinib dropped to approximately 78% of the initial concentration (FIG. 11). Like that in rat plasma, the percentage of the compounds in the invention only slightly dropped to 95% of the initial concentration.

Results from Co-Incubation in Mouse Plasma

Little differentiation was observed between osimertinib and the compounds in the invention after incubating for two hours in mouse plasma, shown in FIG. 12. The small difference in the remaining percentages between 92% (osimertinib) and 96% (the compounds in the invention) is not statistically significant.

Example 3

Cell Viability Studies on F1- and F1-D3-Osimertinib Inhibition of EGFR-179M Activating Mutant NCI-H1975 is a model human NSCLC cell line that expresses activating EGER-T790M mutant, resulting in uncontrolled cell proliferation. Efficient inhibition of EGFR tyrosine kinase activity by TKI can affect cell growth, causing cell death. Here the inventors studied the effect of F1-osimertinib on cell viability of NCI-H1975 cells by LWT-8 assay (Cell Counting Kit-8 (CCK-8), Bimake.com, Houston, Tex.). 4,000 exponentially growing cells in 100 ul culture media were seeded in triplicate into 96-well plates and cultured to 70-80% continency. Cells were treated with indicated concentration of F1-osimertinib for 36 hour. 10 ul/well CCK-8 were added and continuously incubated till the absorbance (OD) at 450 nm reaches 0.8 measured by a microplate reader. Medium only wells were served as blank control. The cell viability was calculated as follows:

Cell viability (%)=[$A$(F1-osimertinib)−$A$(blank)]/[$A$ (solvent)−$A$(blank)]×100%. $A$: OD value measured.

As shown in FIG. 13, the results show significant inhibition of NSCLC cell growth, demonstrating the anti-proliferative effects of F1-osimertinib and F1-D3-osimertinib in NCI-H1975 cells.

While the invention has been described with reference to certain particular embodiments thereof, those skilled in the art will appreciate that various modifications may be made without departing from the spirit and scope of the invention. The scope of the appended claims is not to be limited to the specific embodiments described.

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

REFERENCES

References and citations to other documents, suet as patents, patent applications, patent publications, journals, books, papers, web contents, have been made in this disclosure. All such documents are hereby incorporated herein by reference in their entirety for all purpose. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

What is claimed is:

1. A compound of the following Formula (V) or a pharmaceutically acceptable salt or ester thereof:

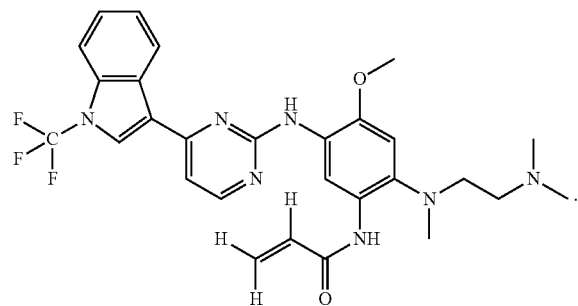

(V)

2. A compound of the following Formula (IX) or a pharmaceutically acceptable salt or ester thereof:

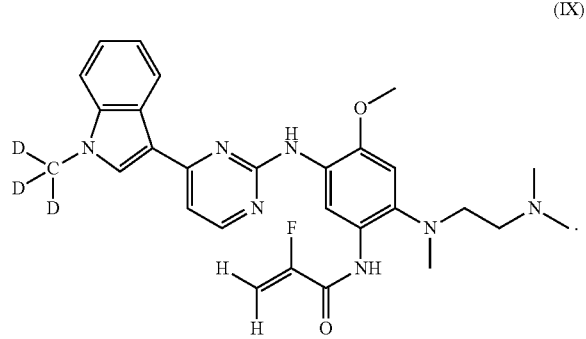 [SMILES: [2H]C([2H])([2H])n1cc(-c2ccnc(Nc3cc(NC(=O)C(F)=C(F)F)c(N(C)CCN(C)C)cc3OC)n2)c2ccccc21]

(IX)

3. A compound of the following Formula (I):

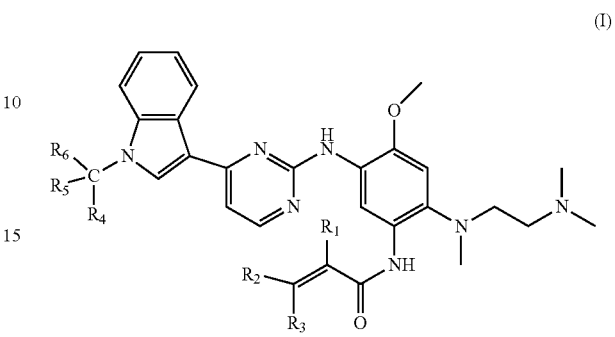

(I)

wherein each of $R_1$, $R_2$, $R_3$, $R_4$, $R_5$ and $R_6$ is independently selected from the group consisting of H, F and D, and at least one of $R_1$, $R_2$, $R_3$, $R_4$, $R_5$ or $R_6$ is F, and wherein the compound is in the form of a mesylate salt.

4. A pharmaceutical composition comprising the compound of claim 3, and a pharmaceutically acceptable excipient, carrier, or diluent.

5. A unit dosage form comprising the pharmaceutical composition of claim 4.

6. The compound of claim 1, wherein the compound is in the form of a mesylate salt.

7. A pharmaceutical composition comprising the compound of claim 1, or a pharmaceutically acceptable salt or ester thereof, and a pharmaceutically acceptable excipient, carrier, or diluent.

8. A unit dosage form comprising the pharmaceutical composition of claim 7.

9. The compound of claim 2, wherein the compound is in the form of a mesylate salt.

10. A pharmaceutical composition comprising the compound of claim 2, or a pharmaceutically acceptable salt or ester thereof, and a pharmaceutically acceptable excipient, carrier, or diluent.

11. A unit dosage form comprising the pharmaceutical composition of claim 10.

12. A pharmaceutical composition comprising the compound of claim 6, and a pharmaceutically acceptable excipient, carrier, or diluent.

13. A unit dosage form comprising the pharmaceutical composition of claim 12.

14. A pharmaceutical composition comprising the compound of claim 9, and a pharmaceutically acceptable excipient, carrier, or diluent.

15. A unit dosage form comprising the pharmaceutical composition of claim 14.

* * * * *